US012121346B2

(12) United States Patent
Fratantonio

(10) Patent No.: US 12,121,346 B2
(45) Date of Patent: Oct. 22, 2024

(54) DENTAL BONDED VENEER IDENTIFICATION DEVICE

(71) Applicant: Nicholas R. Fratantonio, Chesterland, OH (US)

(72) Inventor: Nicholas R. Fratantonio, Chesterland, OH (US)

(*) Notice: Subject to any disclaimer, the term of this patent is extended or adjusted under 35 U.S.C. 154(b) by 0 days.

(21) Appl. No.: 17/907,725

(22) PCT Filed: May 7, 2021

(86) PCT No.: PCT/US2021/031270
§ 371 (c)(1),
(2) Date: Sep. 29, 2022

(87) PCT Pub. No.: WO2021/236358
PCT Pub. Date: Nov. 25, 2021

(65) Prior Publication Data
US 2023/0137552 A1 May 4, 2023

Related U.S. Application Data

(60) Provisional application No. 63/028,603, filed on May 22, 2020.

(51) Int. Cl.
A61B 5/00 (2006.01)
A61B 5/11 (2006.01)

(52) U.S. Cl.
CPC ............ A61B 5/1112 (2013.01); A61B 5/682 (2013.01); A61B 2560/0219 (2013.01)

(58) Field of Classification Search
CPC .................. A61B 5/1112; A61B 5/682; A61B 2560/0219; G06K 19/07758
USPC ..................................... 340/539.13
See application file for complete search history.

(56) References Cited

U.S. PATENT DOCUMENTS

| | | | | |
|---|---|---|---|---|
| 2005/0026113 A1* | 2/2005 | Chen | ...................... | A61B 5/076 433/173 |
| 2008/0169906 A1* | 7/2008 | Joo | .................. | G06K 19/07749 340/10.1 |
| 2009/0237236 A1* | 9/2009 | Maassarani | ............. | G01S 19/39 433/229 |
| 2012/0126948 A1* | 5/2012 | Brunski | ............... | A61B 5/1178 340/10.1 |
| 2015/0170504 A1* | 6/2015 | Jooste | .................. | A61B 5/6802 340/539.12 |
| 2019/0243997 A1* | 8/2019 | Danaei-Moghaddam | .................. | A61B 5/1112 |

(Continued)

FOREIGN PATENT DOCUMENTS

| | | |
|---|---|---|
| JP | 2004258781 A | 9/2004 |
| JP | 2010147536 A | 7/2010 |

OTHER PUBLICATIONS

International Search Report mailed Aug. 31, 2021, for priority International Patent Application No. PCT/US2021/031270.

(Continued)

Primary Examiner — Omar Casillashernandez
(74) Attorney, Agent, or Firm — Renner, Otto, Boisselle & Sklar, LLP

(57) ABSTRACT

A dental veneer is provided herein for supplying identification information. The dental veneer includes circuitry, memory, and an antenna. The circuitry reads and/or writes the identification information to the memory and causes the antenna to transmit the identification information.

20 Claims, 5 Drawing Sheets

(56) References Cited

U.S. PATENT DOCUMENTS

2021/0282650 A1* 9/2021 Yoshida .................. A61C 8/00
2023/0037831 A1* 2/2023 Smolarz ............... H04R 25/606

OTHER PUBLICATIONS

Written Opinion mailed Aug. 31, 2021, for priority International Patent Application No. PCT/US2021/031270.
International Preliminary Report on Patentability completed Jul. 12, 2020, for priority International Patent Application No. PCT/US2021/031270.

* cited by examiner

DENTAL BONDED VENEER IDENTIFICATION DEVICE

This application is a national phase of International Patent Application No. PCT/US2021/031270 filed May 7, 2021, which claims priority to U.S. Provisional Patent Application No. 63/028,603 filed May 22, 2020, each of which is hereby incorporated herein by reference in its entirety.

RELATED APPLICATIONS

This application claims the benefit of 63/028,603 filed on May 22, 2020. Which is herein incorporated by reference in its entirety.

TECHNICAL FIELD

The present disclosure relates generally to dental veneers and more particularly to a dental veneer providing identification information.

BACKGROUND

In the US in 2019, there were over 600,000 missing persons. On average there are between 80,000 and 90,000 missing people in the US at any given time, with many of these people never found. This silent disaster disproportionally affects individuals under 21 and people with Alzheimer's or dementia.

An improved method of identifying individuals and recovery measures is needed to help combat this problem.

SUMMARY

A dental veneer is provided herein for supplying identification information and medical alerts. The dental veneer is affixed to a tooth surface and provides identification information wirelessly.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages, and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

Figure 1:
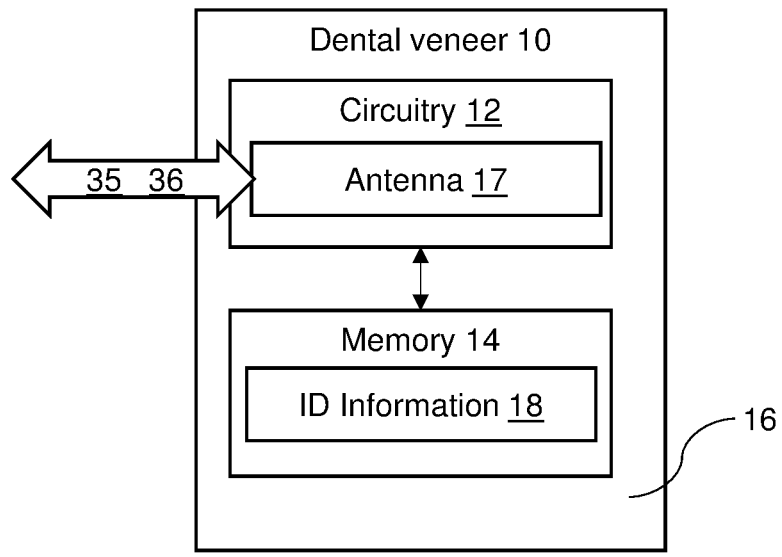
FIG. 1 is a schematic diagram of an exemplary dental veneer.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

According to a general embodiment, a dental veneer is provided for wirelessly providing identification information.

Turning to FIG. 1, a dental veneer 10 for placing in the oral cavity and for supplying identifying information is shown. The dental veneer 10 includes circuitry 12, a non-transitory computer readable medium (memory) 14, and a fastener 16. The circuitry 12 includes an antenna 17 for receiving and/or transmitting wireless signals. The memory 14 is configured to store the identifying information and is communicatively coupled to the circuitry 12, such that information 18 received by the circuitry 12 may be stored in the memory 14 and such that information 18 stored in the memory 14 may be wirelessly transmitted by the circuitry 12. The fastener 16 is configured to maintain a position of the circuitry 12 and the memory 14 within the oral cavity.

Figure 2:
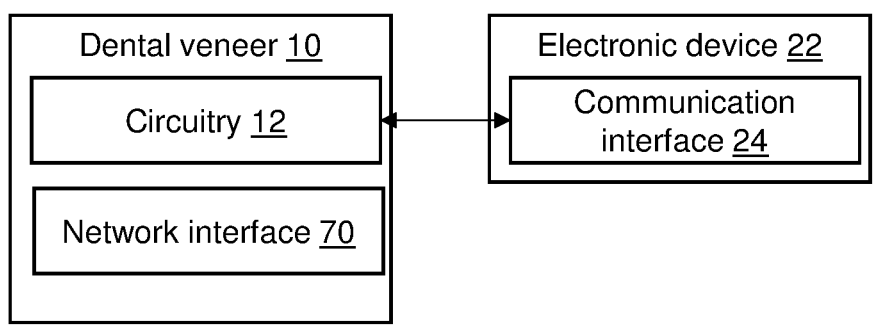
FIG. 2 is a schematic diagram of an exemplary dental veneer system including the dental veneer of FIG. 1.

Turning to FIG. 2, a dental veneer system 20 is shown. The dental veneer system 20 includes the dental veneer 10 and an electronic device 22. The electronic device 22 includes a communication interface 24 for communicating wirelessly with the circuitry 12 of the dental veneer 10.

Figure 3:
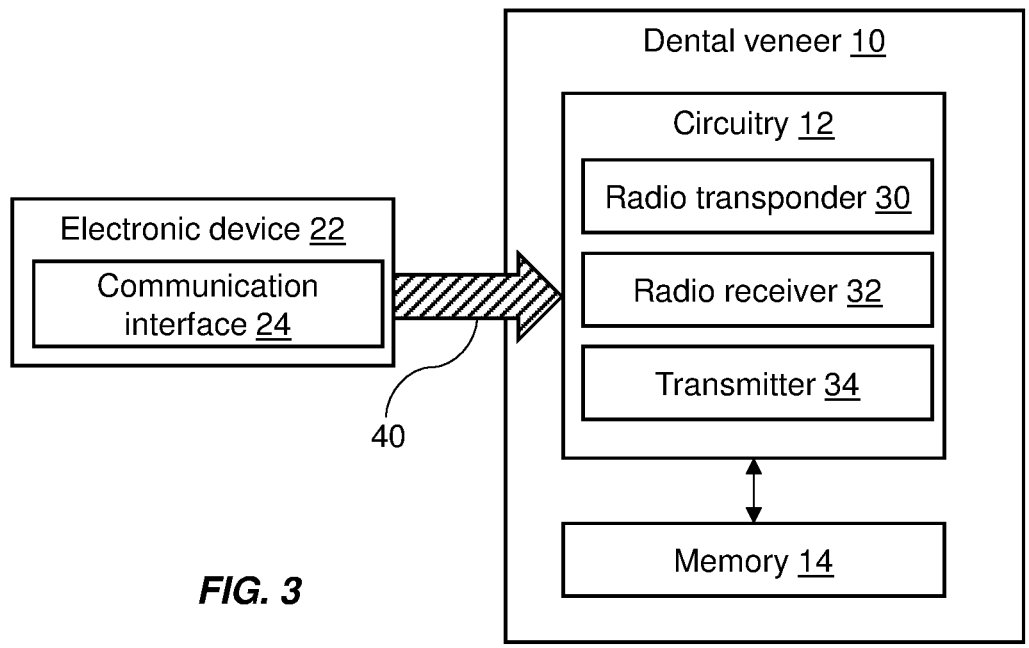
FIG. 3 is a schematic diagram of an exemplary dental veneer including a radio frequency identification (RFID) tag.

The circuitry 12 may take the form of any hardware capable of processing and providing digital information. In one embodiment, the memory 14 stores the identification information 18 and the antenna 17 receives both a request for the identification information 35 and electrical energy 36. The circuitry 12 may cause the antenna 17 to use the received electrical energy to transmit the identification information 18 stored in the memory 14. For example, in the embodiment depicted in FIG. 3, the circuitry 12 includes a radio frequency identification (RFID) tag. In this embodiment, the circuitry 12 includes a radio transponder 30, a radio receiver 32, and a transmitter 34. The circuitry 12 may receive the energy for writing the identification information 18 into the memory 14 and/or wirelessly communicating with the electronic device 22 from interrogation waves generated by the electronic device 22.

The antenna 17 may receive both a request for the identification information 35 and electrical energy 36. In this embodiment, the circuitry 12 causes the identification information 18 to be stored in the memory 14 by using the received electrical energy 36 to write the identification information to the memory 14.

The antenna 17 may be any suitable structure for at least one of receiving identification information 18, requests for identification information 35, or electrical energy 36.

In one embodiment, the electronic device 22 is used to store identification information 18 in the memory 14 of the dental veneer 10. For example, the dental veneer 10 may be received by a user before veneration with no identification information 18 stored in the memory 14. In this state, when the circuitry 12 communicates with the electronic device 22, the circuitry 12 may request the identification information 18. Upon receiving the identification information 18, the circuitry 12 may store the identification information 18 in the memory 14 in a permanent form. As described above, the circuitry 12 may cause the identification information 18 to be stored in the memory 14 by using the received electrical energy 36 to write the identification information 18 to the memory 14. For example, the identification information 18 may be stored in the memory 14 in a read only form. In this example, the identification information 18 may be prevented from being changed by one or more of the circuitry 12 and/or the memory 14.

The identification information 18 may include any desired information. For example, the identification information 18 may include a name, social security number, student identification (ID) number, medical conditions, allergies, security clearance, etc. The identification information 18 may be encrypted when transmitted and/or when stored in the memory 14.

After identification information 18 has been stored in the memory 14, the circuitry 12 may be interrogated to wirelessly provide the identification information 18. For example, upon receiving an electromagnetic interrogation pulse 40 from the electronic device 22, the circuitry 12 may transmit the identification information 18 back to the electronic device 22.

Figure 4:
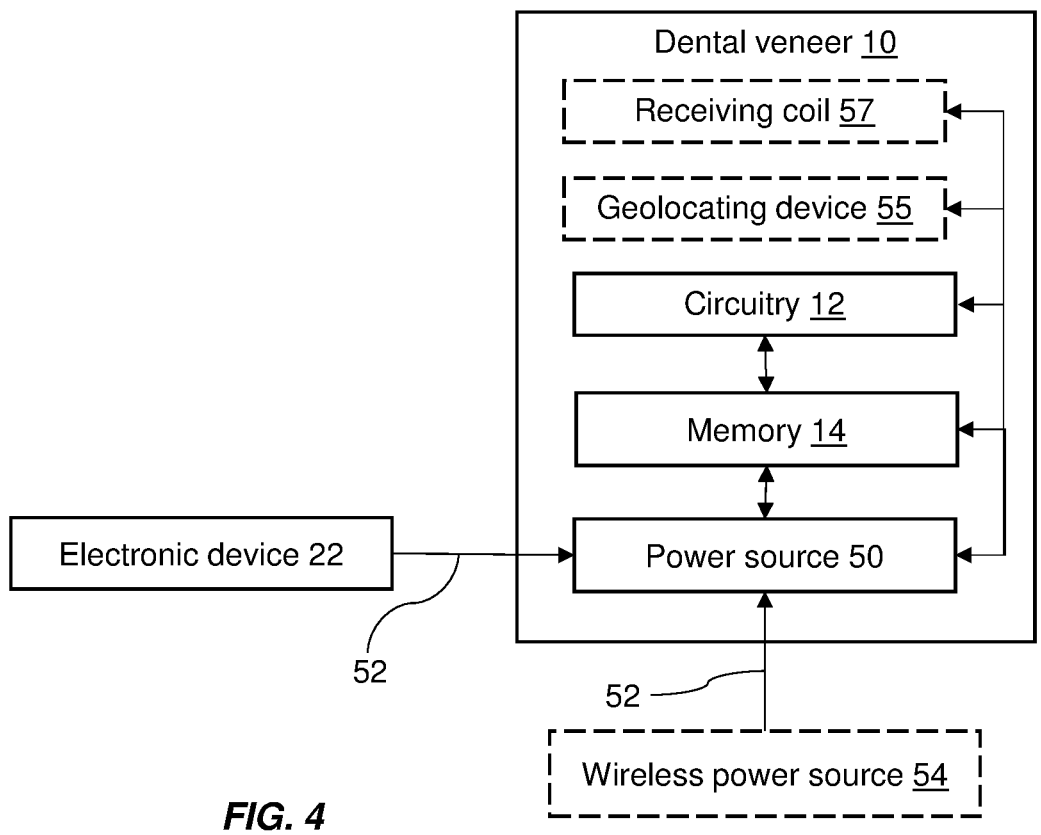
FIG. 4 is a schematic diagram of an exemplary dental veneer including a power source.

In an embodiment where the circuitry 12 includes an RFID tag, the circuitry 12 may take the form a passive RFID tag as described above or alternatively as an active RFID tag as shown in FIG. 4. For example, the dental veneer 10 may additionally include a power source 50 (such as a battery) configured to store electrical energy. The power source 50 may provide the stored electrical energy to at least one of the circuitry 12, antenna 17, or memory 14.

The electrical energy 52 may be wirelessly provided by the electronic device 22 or another wireless power source 54. For example, the wireless power source 54 may generate an inductive or magnetic field for passing the electrical energy 52 to the power source 50. The dental veneer 10 may include a receiving coil 57 for receiving the electrical energy 52 from the inductive or magnetic field.

The wireless power source 54 may be a wireless charger located within a pillow or within a pillowcase. When a user sleeps on the pillow, the pillow may provide electrical energy 52 to the dental veneer 10. In another embodiment, the wireless power source 54 may be a mouth guard including a battery. The mouth guard may be configured to provide wireless power to the dental veneer or via contacts located within the mouth guard and the dental veneer 10. In another embodiment, the dental veneer 10 may be removable (e.g., dentures) and the dental veneer 10 may be removed from the mouth for charging (e.g., plugging the data item 10 into an electrical outlet via a charging cable).

In another embodiment, the dental veneer 10 may include a charger 56 configured to provide the electrical energy 52 to the power source 50. The charger 56 may be any suitable device for generating electrical energy 52. For example, charger 56 may be a piezoelectric charging device. The piezoelectric charging device may use chewing and similar movements to generate the electrical energy for recharging the power source 50.

Figure 5:
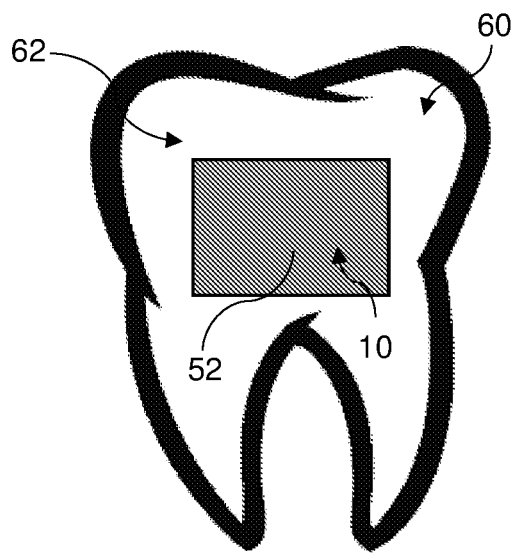
FIG. 5 shows a schematic diagram of a dental veneer adhered to a side of a tooth.

In the embodiment shown in FIG. 5, the dental veneer 10 additionally includes a housing 52. The housing 52 may take the form of a tooth or have a contour configured to conform to a portion of a tooth. The housing 52 may receive the circuitry 12, the antenna 17, and the memory 14. The fastener 16 may maintain the position of the circuitry 12 in the oral cavity by binding the housing to at least one of the tooth or an alveolar bone. In the depicted embodiment, the housing 52 is a flat flexible material configured to conform to a surface that the housing 52 is adhered to. In this embodiment, the housing 52 is molded to a surface 60 of a tooth 62 by the housing 52 being pressed against the surface 60 and the position relative to the tooth surface 60 is maintained using the fastener 16. Alternatively, in another embodiment, the housing 52 may be made from a rigid material that has a contour matching the surface 60 of the tooth 62.

Figure 6:
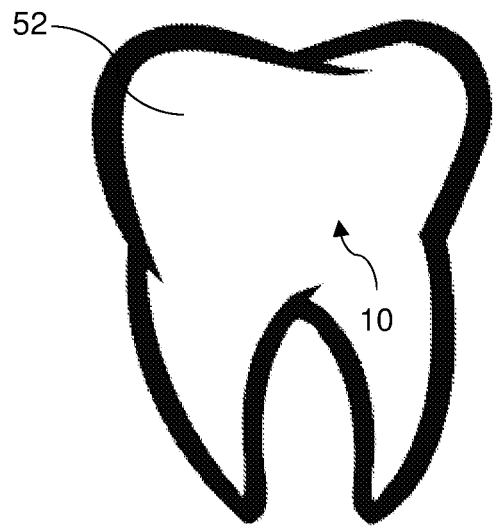
FIG. 6 shows a schematic diagram of a dental veneer embodied as an artificial tooth.
Figure 7:
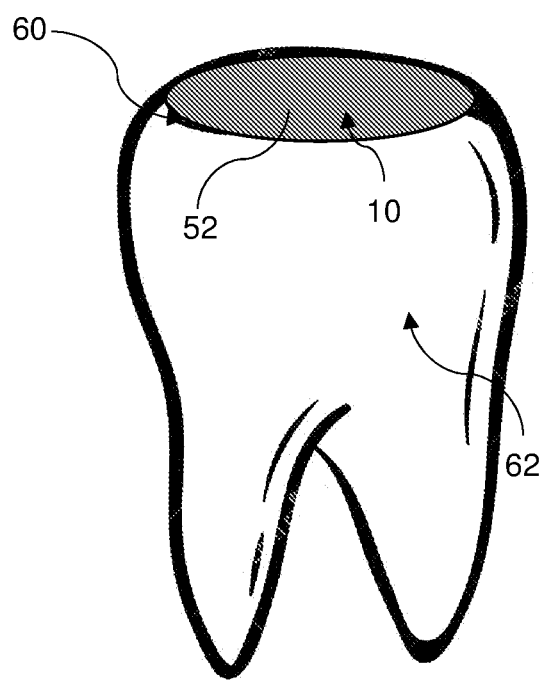
FIG. 7 shows a schematic diagram of a dental veneer embodied as a fixture.

In the embodiment shown in FIG. 6, the housing 52 has the same size and shape as an artificial tooth. In the embodiment shown in FIG. 7, the housing 52 has the same size and shape a as dental filling (e.g., a filling used to treat a cavity). In both of these embodiments, the circuitry 12, memory 14, and power source 50 may be stored within the housing 52. The fastener 16 may be used to maintain a position of the housing 52 within the mouth. The fastener 16 may be any device or object capable of attaching the housing to an object, such that the dental veneer 10 is located within the oral cavity. For example, the fastener 16 may be an adhesive. In one embodiment, the fastener 16 is a dental cement used to attach the housing to a tooth or a bone (such as the alveolar bone).

The dental veneer 10 may be installed by a dentist or may be installed at home. For example, a customer may receive a dental veneer 10 without any identification information 18 stored in the memory 14 or the dental veneer 18 may be received with the customer's identification information 18 already stored in the memory 14. When the dental veneer 18 is received without any stored identification information 18, the customer may use an electronic device (e.g., a smartphone) to provide the identification information 18 to the circuitry 12 for storing in memory 14 as described above. The customer may fix the dental veneer 10 in place using a supplied fastener 16. For example, the customer may use a swab to apply adhesive 16 to a surface of a molar (e.g., a surface adjacent the buccal tissues) and may then stick the housing 52 (including the circuitry 12 and memory 14) to the fastener 16.

The housing 52 may be made of any suitable material for encapsulating the circuitry 12 and memory 14 from the oral cavity. For example, the housing 52 may be made from one or more of gold, amalgam, dental composites, glass ionomer cement, porcelain, ceramic or composite acrylic, etc.

As described above, the fastener 16 may comprise any suitable material for adhering the dental veneer 10 to a tooth 62. For example, the fastener 16 may be a cyanoacrylate adhesive, dental cement, etc.

Figure 9:
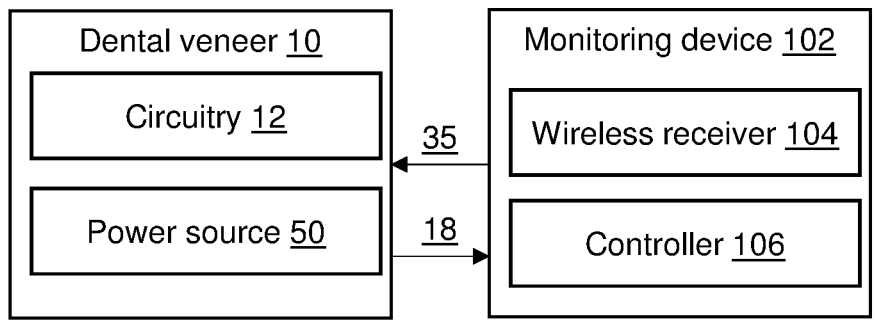
FIG. 9 depicts an embodiment of the security system including a monitoring device.

In the embodiment shown in FIG. 9, a security system 100 for monitoring a patient's location is shown. The security system 100 includes the dental veneer 100 and a monitoring device 102. In a periodic broadcast mode, the circuitry 12 may periodically broadcast at a broadcast frequency at least one of the identification information or the location information. The monitoring device 102 may include a wireless receiver 104 and a controller 106. The wireless receiver 104 detects the periodic broadcast of the identification information. When the periodic broadcast has not been detected by the wireless receiver for an alarm time threshold, the controller 106 issues a notification. The circuitry 12 of the dental veneer 10 may have a periodic broadcast mode.

For example, when the dental veneer 10 is used with an Alzheimer's patient, the circuitry 12 may be configured to transmit identification information at a given frequency (e.g., every five minutes, every fifteen minutes, etc.). Using receiving antennas located within a structure (e.g., a nursing home, residential house, etc.) it may be determined whether the patient having the dental veneer 10 is within the structure. For example, if the receiving antennas do not receive identification information from the dental veneer 10 within a time threshold (e.g., 5 minutes, 15 minutes, 1 hour, etc.), then a signal warning may be sent indicating that the patient is no longer located within the structure. Similarly, an estimated location of the patient within the structure may be determined based on which receiving antenna received the identification information from the dental veneer 10. For example, if the dental veneer has a range of 10 feet and identification information is received by two antennas, then it can be determined that the patient is located within an overlap between two circles having a radius of 10 feet and centered around both antennas.

The monitoring device 102 may be any suitable device for receiving the identification information and sending a notification. For example, the notification may be a warning sent via the internet that the identification information has not been detected within the alarm time threshold (e.g., 15 minutes, 30 minutes, 1 hour, etc.).

In one embodiment including a power source 50, the circuitry 12 may be configured to listen for an interrogation signal. Upon receiving the interrogation signal, the circuitry 12 may transmit the identification information. For example, a security system may include an antenna near each secured doorway for transmitting the interrogation signal and for receiving the identification information. When a user having the dental veneer 10 approaches a secured doorway, the interrogation signal will be received by the dental veneer 10 and the dental veneer 10 will transmit the identification information 18. Upon receiving the identification information 18, the security system may determine whether the user identified by the identification information 18 has access to the secured doorway. If the user has access, then the doorway may be unlocked.

In another embodiment including the power source 50, the dental veneer 10 may also include a geolocating device 55. The geolocating device 55 may be used to determine a geolocation of the dental veneer. The circuitry 12 may then transmit this determined location (e.g., via the antenna 17). Due to power requirements of geolocating devices 55, the circuitry 12 may be configured to only request a physical location from the geolocating device 55 when the circuitry 12 has not received an externally derived location signal (also referred to as a home signal). For example, a patient's residence may include antennas for generating the externally derived location signal (indicating that the patient is at home) that is received by the circuitry 12. If the circuitry 12 does not receive a home signal for a period of time (e.g., 1 hour), then the circuitry 12 may request a geolocation from the geolocating device 55. Upon receiving the geolocation from the geolocating device 55, the circuitry 12 may broadcast the determined location (e.g., via an internet modem located within the dental veneer).

The geolocating device 55 may be any suitable device for determining a location. For example, the geolocating device 55 may be a Global Positioning System (GPS) chip.

In one embodiment, the dental veneer 10 includes a network interface 70 configured to communicate wirelessly with the electronic device 22. For example, the network interface 24 may communicate via Bluetooth or WIFI with the electronic device 22. The electronic device 22 may receive location information and/or identification information from the dental veneer 10 (e.g., via a GPS chip of the dental veneer 10) or the electronic device 22 may use location information from a source external from the dental veneer 10 (e.g., via a GPS chip of the electronic device). The electronic device 22 may then communicate a location of the dental veneer 10 to a server (e.g., via the internet). In one embodiment, the electronic device 22 may execute an application that controls sending of the location information to the server.

In one embodiment, the dental veneer 10 may receive a signal (e.g., from the electronic device 22) for activating or deactivating operating modes of the dental veneer 10. For example, in embodiments including a GPS chip, the dental veneer 10 may deactivate use of the GPS chip (e.g., to reduce electrical power use).

Figure 8:
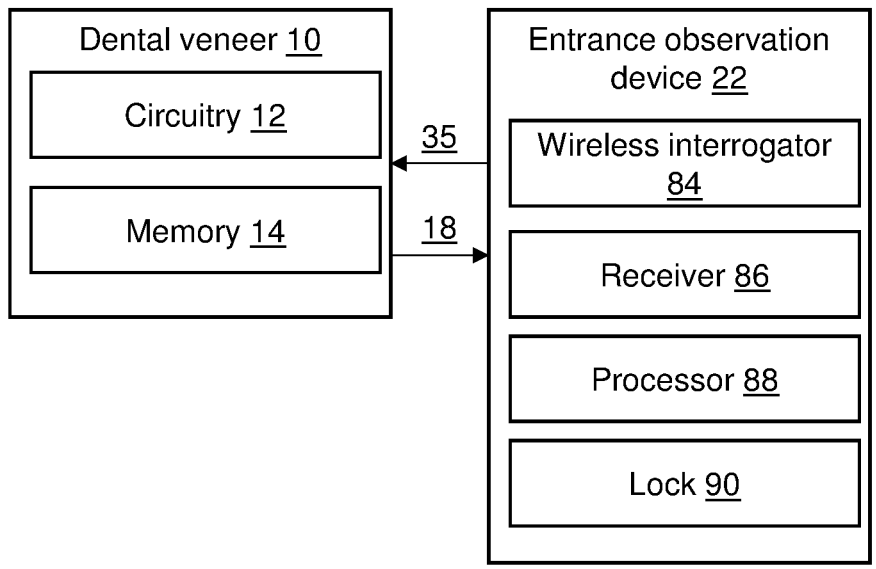
FIG. 8 depicts an embodiment of a security system including the dental veneer and an entrance observation device.

In the embodiment shown in FIG. 8, a security system 80 for monitoring a patient's location is shown. The security system includes the dental veneer 10 and an entrance observation device 82. The entrance observation device 82 includes a wireless interrogator 84 and a receiver 86. The wireless interrogator 84 outputs a request for the identification information 35 and the receiver 86 receives the transmitted identification information 18. For example, the entrance observation device 82 may be positioned at an entrance or exit from an area (e.g., a door). The wireless interrogator 84 and receiver 86 may be embodied as any wireless communication device capable of sending a request for the identification information 35 and for receiving the identification information 18.

The entrance observation device 82 may also include a processor 88 and a lock 90. The processor 88 may disengage the lock 90 when the received identification information 18 matches an approved identity. For example, the processor 88 may receive from a memory (not shown) a list of approved identities. The processor 88 may then compare the received identification information to the list of approved identities.

Figure 10:
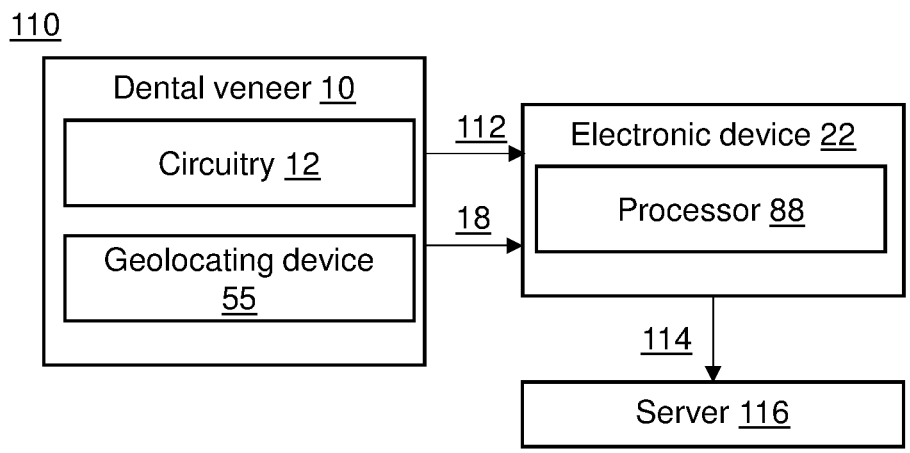
FIG. 10 depicts an embodiment of a monitoring system including the dental veneer and an electronic device.

In the embodiment shown in FIG. 10, a monitoring system 110 is shown. The monitoring system 110 includes the dental veneer 10 and the electronic device 22. The electronic device 22 receives from the dental veneer 10 at least one of the identification information 18 or the location information 112. The electronic device 22 may transmit a notification 114 to a server 116 based on the received at least one identification information 18 or location information 112.

Figure 11:
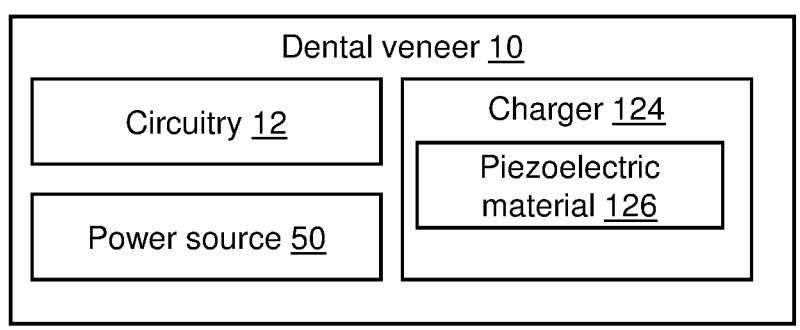
FIG. 11 depicts an embodiment of a dental veneer including a charger.

In the embodiment shown in FIG. 11, the dental veneer 10 includes a charger 124. The charger 124 both generates electrical energy and supplies the generated electrical energy to the power source 50. The charger 124 may be any device capable of generating electrical energy. For example, the charger 124 may include a piezoelectric material 126 configured to generate the electrical energy.

The circuitry 12, processor 88, and controller 106 may each have various implementations. For example, the circuitry 12, processor 88, and controller 106 may each include any suitable device, such as a processor (e.g., CPU), programmable circuit, integrated circuit, memory and I/O circuits, an application specific integrated circuit, microcontroller, complex programmable logic device, other programmable circuits, or the like. The circuitry 12, processor 88, and controller 106 may each also include a non-transitory computer readable medium, such as random-access memory (RAM), a read-only memory (ROM), an erasable programmable read-only memory (EPROM or Flash memory), or any other suitable medium. Instructions for performing the method described below may be stored in the non-transitory computer readable medium and executed by the circuitry 12, processor 88, and controller 106. The circuitry 12, processor 88, and controller 106 may each be communicatively coupled to the computer readable medium and network interface through a system bus, mother board, or using any other suitable structure known in the art.

As will be understood by one of ordinary skill in the art, the computer readable medium (memory) 14 may be, for example, one or more of a buffer, a flash memory, a hard drive, a removable media, a volatile memory, a non-volatile memory, a random-access memory (RAM), or other suitable device. In a typical arrangement, the computer readable medium 14 may include a non-volatile memory for long term data storage and a volatile memory that functions as system memory for the processor 14. The computer readable medium 14 may exchange data with the circuitry over a data bus. Accompanying control lines and an address bus between the computer readable medium 14 and the circuitry also may be present. The computer readable medium 14 is considered a non-transitory computer readable medium.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A dental veneer for placing in the oral cavity and for supplying identifying information, the dental veneer comprising:
    circuitry including an antenna configured to at least one of receive or transmit wireless signals;
    a power source configured to store electrical energy and provide the stored electrical energy to the circuitry;
    a non-transitory computer readable memory configured to store the identifying information, wherein;
        the memory is communicatively coupled to the circuitry; and
        upon receiving an electromagnetic interrogation pulse from an electronic device in an entryway, the circuitry is further configured to transmit the stored identifying information to the electronic device via the antenna; and
    a fastener configured to maintain a position of the circuitry, the power source, and the memory within the oral cavity.

2. The dental veneer of claim 1,
    wherein:
        the antenna is configured to receive both a request for the identification information and electrical energy from the power source; and
        the circuitry is configured to cause the antenna to use the received electrical energy to transmit the identification information stored in the memory.

3. The dental veneer of claim 1, further comprising a geolocating device configured to output a geolocation of the geolocating device, wherein the circuitry is configured to receive the geolocation from the geolocating device and to transmit the geolocation via the antenna.

4. The dental veneer of claim 3, wherein the circuitry is further configured to:
    receive an externally derived location signal via the antenna; and
    when the circuitry has not received the externally derived location signal for a time duration, request the geolocation from the geolocating device.

5. The dental veneer of any of claim 3, wherein the circuitry is further configured to periodically broadcast at a broadcast frequency at least one of the identification information or the location information.

6. The dental veneer of claim 3, further comprising a network interface configured to:
    communicate with an electronic device; and
    transmit at least one of the identification information or the location information to the electronic device.

7. A monitoring system comprising:
    a dental veneer for placing in the oral cavity and for supplying identifying information, the dental veneer comprising:
        a power source configured to store electrical energy;
        circuitry including an antenna configured to at least one of receive or transmit wireless signals and to receive electrical energy from the power source;
        a non-transitory computer readable memory configured to store the identifying information;
        a fastener configured to maintain a position of the circuitry and the memory within the oral cavity; and
        a network interface, wherein the memory is communicatively coupled to the circuitry and to the network interface; and
    an electronic device in an entryway configured to:
        communicate with the network interface of the dental veneer and communicate to a server a location of the dental veneer with respect to the entryway;
        transmit an electromagnetic interrogation pulse to the dental veneer, wherein the circuitry is configured to cause the network interface to transmit the identifying information to the electronic device;
        receive from the dental veneer the identification information; and
        transmit a notification to a server based on the received identification information.

8. The dental veneer of claim 1, further comprising a charger configured both to generate electrical energy and to supply the generated electrical energy to the power source.

9. The dental veneer of claim 8, wherein the charger includes a piezoelectric material configured to generate the electrical energy.

10. The dental veneer of claim 1, further comprising a housing having a shape of a tooth or having a contour configured to conform to a portion of the tooth.

11. The dental veneer of claim 10, wherein:
the housing is configured to receive the circuitry, the antenna, the power source, and the memory; and
the fastener maintains the position of the circuitry in the oral cavity by binding the housing to at least one of the tooth or an alveolar bone.

12. The dental veneer of claim 1, wherein the circuitry includes a radio frequency identification (RFID) tag.

13. The dental veneer of claim 1, wherein the identification information includes at least one of a name, social security number, student identification (ID) number, medical condition, allergy, or security clearance.

14. The dental veneer of any of claim 2, wherein the power source is configured to receive electrical energy from a wireless power source.

15. The dental veneer of claim 14, wherein the dental veneer further includes a receiving coil for receiving the electrical energy from an inductive or magnetic field generated by the wireless power source.

16. A monitoring system comprising:
a dental veneer for placing in the oral cavity and for supplying identifying information, the dental veneer comprising:
a power source configured to store electrical energy;
circuitry including an antenna configured to at least one of receive or transmit wireless signals and to receive electrical energy from the power source;
a non-transitory computer readable memory configured to store the identifying information;
a fastener configured to maintain a position of the circuitry and the memory within the oral cavity; and
a network interface, wherein the memory is communicatively coupled to the circuitry and to the network interface; and
an electronic device in an entryway configured to communicate with the network interface of the dental veneer;
where the electronic device is configured to transmit an electromagnetic interrogation pulse;
wherein the circuitry is configured to cause the network interface to transmit the identifying information to electronic device;
wherein the electronic device is configured to communicate to a server a location of the dental veneer with respect to the entryway.

17. The monitoring system of claim 16, wherein the electronic device further comprises an application that controls sending of the location of the dental veneer to the server; and wherein the electronic device executes the application to communicate the location of the dental veneer to the server.

18. The monitoring system of claim 16, wherein the dental veneer further comprises a global positioning system (GPS) chip; wherein the GPS chip provides location information indicating the location of the dental veneer; wherein the network interface is configured to transmit the location information to the electronic device; and wherein the electronic device is configured to receive from the dental veneer the location information indicating the location of the dental veneer.

19. The monitoring system of claim 16, wherein the electronic device further comprises a global positioning system (GPS) chip; and wherein the GPS chip provides location information indicating the location of the dental veneer.

20. A security system for monitoring a patient's location, the security system comprising:
a dental veneer for placing in the oral cavity and for supplying identifying information, the dental veneer comprising:
a power source configured to store electrical energy; and
circuitry including an antenna configured to at least one of receive or transmit wireless signals;
wherein the circuitry is configured to receive electrical energy from the power source; and
wherein the circuitry is configured to periodically broadcast at a broadcast frequency the identification information;
a non-transitory computer readable memory configured to store the identifying information; and
a fastener configured to maintain a position of the circuitry and the memory within the oral cavity; and
a monitoring device in en entryway including:
a wireless receiver configured to detect at the entryway the periodic broadcast of the identification information; and
a controller configured to: when the periodic broadcast has not been detected by the wireless receiver for an alarm time threshold, issue a notification indicating the dental veneer is no longer in contact with the wireless receiver.

* * * * *